(12) United States Patent
Mimitsuka et al.

(10) Patent No.: US 8,871,477 B2
(45) Date of Patent: Oct. 28, 2014

(54) PROCESS FOR PRODUCTION OF CADAVERINE

(75) Inventors: Takashi Mimitsuka, Kamakura (JP); Kazumi Suda, Kamakura (JP); Hideki Sawai, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 13/580,742

(22) PCT Filed: Feb. 22, 2011

(86) PCT No.: PCT/JP2011/053764
§ 371 (c)(1),
(2), (4) Date: Nov. 19, 2012

(87) PCT Pub. No.: WO2011/105344
PCT Pub. Date: Sep. 1, 2011

(65) Prior Publication Data
US 2013/0095534 A1    Apr. 18, 2013

(30) Foreign Application Priority Data

Feb. 23, 2010  (JP) ................................ 2010-037043
Aug. 23, 2010  (JP) ................................ 2010-186034

(51) Int. Cl.
*C12P 13/00* (2006.01)

(52) U.S. Cl.
CPC .................................... *C12P 13/001* (2013.01)
USPC ....................................................... 435/128

(58) Field of Classification Search
CPC ....................................................... C12Q 1/689
USPC ....................................... 435/128, 243, 252.3
See application file for complete search history.

(56) References Cited

U.S. PATENT DOCUMENTS

| 7,252,972 | B2 * | 8/2007 | Kikuchi et al. ............... 435/69.8 |
| 2002/0004483 | A1 * | 1/2002 | Nissen et al. .................... 514/12 |
| 2002/0197605 | A1 * | 12/2002 | Nakagawa et al. ............... 435/6 |
| 2003/0219870 | A1 | 11/2003 | Georgiou et al. |
| 2004/0171023 | A1 | 9/2004 | Caimi et al. |
| 2007/0184525 | A1 * | 8/2007 | Date et al. .................... 435/69.1 |
| 2011/0039313 | A1 * | 2/2011 | Verseck et al. ................ 435/128 |
| 2012/0295317 | A1 * | 11/2012 | Schroder et al. .............. 435/128 |

FOREIGN PATENT DOCUMENTS

| JP | 2002-223770 A | 8/2002 |
| JP | 2004-000114 A | 1/2004 |
| JP | 2004-222569 A | 8/2004 |
| JP | 2004-298033 A | 10/2004 |
| JP | 2005-520569 A | 7/2005 |
| JP | 2006-504412 A | 2/2006 |
| JP | 2008-104453 A | 5/2008 |
| JP | 2009-028045 A | 2/2009 |
| JP | 2009-29872 A | 2/2009 |
| JP | 2009-207495 A | 9/2009 |
| JP | 2009-531042 A | 9/2009 |
| WO | 02/081694 A1 | 10/2002 |
| WO | 2004/078951 A1 | 9/2004 |
| WO | 2005/103278 A1 | 11/2005 |
| WO | 2008/092720 A1 | 8/2008 |
| WO | 2009/036067 A2 | 3/2009 |

OTHER PUBLICATIONS

Tateno et al., Direct production of cadaverine from soluble starch using Corynebacterium glutamicum coexpressing α-amylase and lysine decarboxylase. Appl. Microbiol. Biotechnol. 82:115-121, 2009.*

* cited by examiner

*Primary Examiner* — Tekchand Saidha
*Assistant Examiner* — Rama P Ramanujam
(74) *Attorney, Agent, or Firm* — DLA Piper LLP (US)

(57) ABSTRACT

By a method for producing cadaverine by culturing a microorganism that extracellularly secretes lysine decarboxylase, by-production of lysine is suppressed, the yield of cadaverine relative to glucose consumption is improved compared to conventional production methods, and further, the load on the purification step in purification of cadaverine as a raw material for polyamide can be reduced.

11 Claims, No Drawings

PROCESS FOR PRODUCTION OF CADAVERINE

RELATED APPLICATIONS

This is a §371 of International Application No. PCT/JP2011/053764, with an international filing date of Feb. 22, 2011 (WO 2011/105344 A1, published Sep. 1, 2011), which is based on Japanese Patent Application No. 2010-037043, filed Feb. 23, 2010 and Japanese Patent Application No. 2010-186034, filed Aug. 23, 2010, the subject matter of which is incorporated herein by reference.

SEQUENCE LISTING

This application contains a Sequence Listing which has been submitted in ASCII format via EFS-Web and is hereby incorporated by reference in its entirety. Said ASCII copy, created on Dec. 14, 2012, is named TAN12129.txt and is 21,835 bytes in size.

TECHNICAL FIELD

This disclosure relates to a method for producing cadaverine. The disclosure relates especially to a method for efficient production of cadaverine by allowing secretory production of lysine decarboxylase by a microorganism.

BACKGROUND

Polyamide (PA) is a group of important polymers that are used as raw materials for a series of special plastics to be used in the automobile industry, sports industry and lifestyle industry, and diamines are important raw material monomer components for the polyamides. Diamines are condensed with dicarboxylic acids to form various polymers, and the properties of the polymers vary depending on the chain lengths of the diamines and the dicarboxylic acids.

Conventionally, diamines are chemically produced from materials derived from petroleum via dicarboxylic acids at an intermediate stage, or produced by chemical decarboxylation reaction of amino acids Suyama and Kaneo. *Yakugaku Zasshi* (1965), Vol. 85, pp. 513-533. In consideration of sharp rise in oil prices, the methods of synthesis of diamines are preferably switched to methods based on biotechnological processes such as enzyme reactions and microorganism culture, wherein renewable resources are utilized.

In view of this, recent interest has focused on cadaverine as a diamine which can be produced by biotechnological processes. Cadaverine is also called 1,5-pentanediamine, and is a compound that can be a raw material monomer for polyamide. Cadaverine is a biogenic amine which ubiquitously exists in the living body and its biosynthetic system is being elucidated (see Celia White Tabor and a colleague. *Microbiological Reviews* (1985), Vol. 49, pp. 81-99). In a part of its biosynthetic pathway, lysine decarboxylase (LDC) that catalyzes decarboxylation of lysine into cadaverine is known to be involved. As an LDC gene, the *E. coli* (*Escherichia coli*)-derived LDC gene is known (see Shi-Yuan Meng and a colleague. *Journal of Bacteriology* (1992), Vol. 174, pp. 2659-2669).

The conventional biotechnological methods for producing cadaverine are based on introduction of an LDC gene into a microorganism, and can be roughly classified into production methods by enzyme reaction using lysine as a substrate and methods for producing cadaverine by microorganism culture. Further, known examples of the methods for producing cadaverine by microorganism culture include a production method by culturing recombinant *E. coli* (see JP 2002-223770 A), a method wherein the capacity of a coryneform bacterium, which is a lysine-producing microorganism, to produce lysine is further enhanced (see JP 2004-222569 A), a method wherein the cadaverine degradation system is blocked (see Japanese Translated PCT Patent Application Laid-open No. 2009-531042) and a method wherein the lysine transporter is blocked (see WO 2008/092720). However, there are many problems to be solved especially in the methods for producing cadaverine by microorganism culture, and examples of such problems include by-production of lysine in cases of culture of a microorganism prepared by introduction of an LDC gene to a coryneform bacterium, which is a lysine-producing microorganism (see Takashi Mimitsuka and four colleagues. *Bioscience, Biotechnology, and Biochemistry* (2007), Vol. 71, pp. 2130-2135). By-production of lysine prevents improvement of the yield of cadaverine even with successful production of its precursor. Further, since cadaverine needs to be highly purified in order to be used as a raw material for polyamide, By-production of lysine increases the load on purification of cadaverine, which has been economically problematic.

It could therefore be helpful to provide a method for producing cadaverine by culturing a microorganism, which method does not allow lysine as a precursor of cadaverine to remain in the microorganism culture liquid upon completion of culturing of the microorganism.

SUMMARY

We discovered that, by culturing a microorganism that extracellularly secretes lysine decarboxylase, remaining of lysine in the culture liquid upon completion of culturing of a microorganism can be prevented. We thus provide:

(1) A method for producing cadaverine, the method comprising culturing a microorganism that extracellularly secretes lysine decarboxylase.

(2) The method for producing cadaverine according to (1), wherein lysine is added to a medium for culturing the microorganism.

(3) The method for producing cadaverine according to (1) or (2), wherein the microorganism intracellularly expresses a protein comprising lysine decarboxylase having a secretory signal peptide attached to the N-terminus side of the amino acid sequence thereof, which lysine decarboxylase is thereby extracellularly secreted.

(4) The method for producing cadaverine according to (3), wherein the microorganism has a gene construct comprising, in the direction from 5' to 3' of the nucleic acid sequence, a promoter sequence that functions in the microorganism, a nucleic acid sequence encoding the secretory signal peptide and a nucleic acid sequence encoding lysine decarboxylase, which gene construct allows intracellular expression of the protein comprising lysine decarboxylase having a secretory signal peptide attached to the N-terminus side of the amino acid sequence thereof.

(5) The method for producing cadaverine according to (3) or (4), wherein the secretory signal peptide is a peptide represented by the amino acid sequence shown in any of SEQ ID NOs: 13 to 43.

(6) The method for producing cadaverine according to any of (1) to (5), wherein the lysine decarboxylase is derived from *E. coli*.

(7) The method for producing cadaverine according to any of (1) to (6), wherein the microorganism is a coryneform bacterium or *E. coli*.

In our method for producing cadaverine by culturing a microorganism, lysine does not remain in the culture liquid upon completion of culturing of the microorganism so that the yield of cadaverine relative to glucose consumption is improved compared to conventional production methods. Further, the load on the purification step in purification of cadaverine as a raw material for polyamide can be reduced.

DETAILED DESCRIPTION

Our method produces cadaverine by culturing a microorganism that extracellularly secretes lysine decarboxylase. Extracellular "secretion" of lysine decarboxylase means that lysine decarboxylase is transported to the outside of the microorganism (outside of the cell) and finally put into the completely free state in the medium or culture liquid. Cases where only a part of lysine decarboxylase exists in the outside of the cell and cases where lysine decarboxylase is bound to the surface of the microorganism are not included in "secretion."

No microorganism is so far known to extracellularly secrete lysine decarboxylase, but it is possible to allow a desired microorganism to extracellularly secrete lysine decarboxylase by using the genetic engineering technique. More particularly, extracellular secretion of lysine decarboxylase can be achieved by a method that allows intracellular expression of a protein comprising lysine decarboxylase having a secretory signal peptide attached to the N-terminus side of the amino acid sequence thereof.

The lysine decarboxylase is not restricted, and is preferably L-lysine decarboxylase. The origin of the lysine decarboxylase is also not restricted, and preferred examples of the lysine decarboxylase include those derived from *Bacillus halodurans*, *Bacillus subtilis*, *Escherichia coli*, *Selenomonas ruminantium*, *Vibrio cholerae*, *Vibrio parahaemolyticus*, *Streptomyces coelicolor*, *Streptomyces pilosus*, *Eikenella corrodens*, *Eubacterium acidaminophilum*, *Salmonella typhimurium*, *Hafnia alvei*, *Neisseria meningitidis*, *Thermoplasma acidophilum* and *Pyrococcus abyssi*. The lysine decarboxylase is more preferably the one derived from *E. coli*, whose safety has been confirmed. The amino acid sequences of these lysine decarboxylases are registered in a database (GenBank).

A secretory signal peptide was originally discovered as a signal peptide sequence which functions to allow extracellular secretion of a secretory protein. A secretory protein is generally translated as a prepeptide or prepropeptide and then becomes a mature protein. It is known that, after the translation of the protein as a prepeptide or prepropeptide, a secretory signal peptide ("pre portion") is cleaved out by a protease (commonly called signal peptidase) to convert the peptide to a mature peptide or propeptide, which propeptide further undergoes cleaving out of the pro portion by a protease to become a mature peptide, followed by being extracellularly secreted. It is known that a secretory signal peptide has a function to allow not only extracellular secretion of a secretory protein, but also extracellular secretion of a non-secretory protein in cases where the non-secretory protein is fused with the secretory signal peptide. In the present invention, by fusing lysine decarboxylase with a secretory signal peptide, the lysine decarboxylase can be made to be efficiently extracellularly secreted.

The secretory signal peptide may be derived from either a different microorganism or the microorganism to be used, and the secretory signal peptide is preferably derived from the microorganism to be used. Further, the secretory signal peptide may comprise a part of the N-terminal amino acid sequence of the naturally occurring mature protein from which the peptide was derived. Concrete examples of the secretory signal peptide include:

secretory signal peptides such as TorA (trimethylamine N-oxidoreductase) and SufI (Suppressor of ftsI; ftsI suppressor) derived from *E. coli*; PhoD (phosphoesterase) and LipA (lipase) derived from *Bacillus subtilis*; and isomaltodextranase (IMD) derived from *Arthrobacter globiformis* (see SEQ ID NOs: 13 to 17, respectively);

the secretory signal peptide described in JP 3711658 B (see SEQ ID NO:18);

CgR0079, CgR0120, CgR0124, CgR0900, CgR0949, CgR1023, CgR1448, CgR2137, CgR2677, CgR2926, CgR0040, CgR0789, CgR0865, CgR1522, CgR1819, CgR2213, CgR2386 and CgR2535, which are secretory signal peptides derived from *Corynebacterium glutamicum* R described in Microbiology (2009), 155, pp. 741-750 (see SEQ ID NOs: 19 to 36, respectively);

the secretory signal peptide described in JP 9-316095 A (see SEQ ID NO:37);

the signal peptide for arpE, which is the secretory signal for subtilisin, described in Applied and Environmental Microbiology (1995), 61(4), pp. 1610-1613 (see SEQ ID NO:38);

the secretory signal peptide described in Applied and Environmental Microbiology (2003), 69(1), pp. 358-366 (see SEQ ID NO:39); and the secretory signal peptides described in Trends in Microbiology (2005), 13(4), pp. 175-180 (see SEQ ID NOs: 40 to 43).

Examples of the lysine decarboxylase and the secretory signal peptide also include proteins having the same amino acid sequences as those described above except that one or several amino acids are substituted, deleted, inserted and/or added, as long as their functions are maintained. The term "several" herein means normally about 1 to 7, preferably about 1 to 5, especially preferably about 1 to 2. Each of the lysine decarboxylase and the secretory signal peptide may be a protein having an amino acid sequence with a sequence identity of normally not less than 85%, preferably not less than 90%, more preferably not less than 95% to the original amino acid sequence, as long as its functions is maintained.

The substitution(s), deletion(s), insertion(s) and/or addition(s) in the amino acid sequence described above is/are preferably a conservative substitution(s). Examples of conservative substitution of the original amino acid for another amino acid include substitution of Ala for Ser or Thr; substitution of Arg for Gln, His or Lys; substitution of Asn for Glu, Gln, Lys, His or Asp; substitution of Asp for Asn, Glu or Gln; substitution of Cys for Ser or Ala; substitution of Gln for Asn, Glu, Lys, His, Asp or Arg; substitution of Glu for Asn, Gln, Lys or Asp; substitution of Gly for Pro; substitution of His for Asn, Lys, Gln, Arg or Tyr; substitution of Ile for Leu, Met, Val or Phe; substitution of Leu for Ile, Met, Val or Phe; substitution of Lys for Asn, Glu, Gln, His or Arg; substitution of Met for Ile, Leu, Val or Phe; substitution of Phe for Trp, Tyr, Met, Ile or Leu; substitution of Ser for Thr or Ala; substitution of Thr for Ser or Ala; substitution of Trp for Phe or Tyr; substitution of Tyr for His, Phe or Trp; and substitution of Val for Met, Ile or Leu.

Examples of the method for allowing, by genetic recombination, a microorganism to intracellularly express a protein comprising lysine decarboxylase having a secretory signal peptide attached to the N-terminus side of the amino acid sequence thereof include a method wherein a gene construct comprising, in the direction from 5' to 3' of the nucleic acid sequence, a promoter sequence that functions in the microorganism, a nucleic acid sequence encoding a secretory signal peptide and a nucleic acid sequence encoding lysine decarboxylase is introduced to a microorganism.

The promoter is not restricted, and any promoter sequence can be generally used as long as it can function in the microorganism employed. Further, the promoter may be one derived from a different species. Preferred examples of the promoter include:

promoters involved in various amino acid biosynthetic systems, such as the promoters of the glutamate dehydrogenase gene involved in the glutamic acid biosynthetic system; glutamine synthetase gene involved in the glutamine biosynthetic system; aspartokinase gene involved in the lysine biosynthetic system; homoserine dehydrogenase gene involved in the threonine biosynthetic system; acetohydroxy acid synthetase gene involved in the isoleucine and valine biosynthetic systems; 2-isopropyl malic acid synthetase gene involved in the leucine biosynthetic system; glutamate kinase gene involved in the proline and arginine biosynthetic systems; phosphoribosyl-ATP pyrophosphorylase gene involved in the histidine biosynthetic system; and deoxy arabino heptulosonate phosphate (DAHP) synthase gene involved in the biosynthetic systems of aromatic amino acids such as tryptophan, tyrosine and phenylalanine;

promoters involved in the biosynthetic systems of nucleic acids such as inosinic acid and guanylic acid, including the promoters for the phosphoribosyl pyrophosphate (PRPP) amidotransferase gene, inosinic acid dehydrogenase gene and guanylic acid synthetase gene; and strong promoters such as the tac promoter.
The sequences of these promoters are registered in the database (GenBank).

The nucleic acid sequence encoding the secretory signal peptide is not restricted as long as the sequence can be translated into the above-described secretory signal peptide. The nucleic acid sequence can be determined by reference to the codons (standard genetic codes) for the amino acid sequence of the secretory signal peptide (see Horton. Biochemistry, 3rd Edition, Tokyo Kagaku Dojin, p. 526), and, in this process, the nucleic acid sequence may be redesigned with codons frequently used in the microorganism used in the present invention. Concrete examples of the nucleic acid sequence include:

nucleic acid sequences encoding secretory signal peptides such as TorA (trimethylamine N-oxidoreductase) and SufI (Suppressor of ftsI; ftsI suppressor) derived from *E. coli*; PhoD (phosphoesterase) and LipA (lipase) derived from *Bacillus subtilis*; and isomaltodextranase (IMD) derived from *Arthrobacter globiformis* (see SEQ ID NOs: 44 to 48, respectively);

nucleic acid sequences encoding the secretory signal peptide described in JP 3711658 B (see SEQ ID NO:49);

nucleic acid sequences encoding CgR0079, CgR0120, CgR0124, CgR0900, CgR0949, CgR1023, CgR1448, CgR2137, CgR2677, CgR2926, CgR0040, CgR0789, CgR0865, CgR1522, CgR1819, CgR2213, CgR2386 and CgR2535, which are the secretory signal peptides derived from *Corynebacterium glutamicum* R described in Microbiology (2009), 155, pp. 741-750 (see SEQ ID NOs: 50 to 67, respectively);

nucleic acid sequences encoding the secretory signal peptide described in JP 9-316095 A (see SEQ ID NO:68);

nucleic acid sequences encoding the secretory signal peptide described in Applied and Environmental Microbiology (1995), 61(4), pp. 1610-1613 (see SEQ ID NO:69);

nucleic acid sequences encoding the secretory signal peptide described in Applied and Environmental Microbiology (2003), 69(1), pp. 358-366 (see SEQ ID NO:70); and nucleic acid sequences encoding the secretory signal peptides described in Trends in Microbiology (2005), 13(4), pp. 175-180 (see SEQ ID NOs: 71 to 74).

Concrete examples of the nucleic acid sequence encoding the lysine decarboxylase include nucleic acid sequences encoding the lysine decarboxylases derived from the above-described organisms, which nucleic acid sequences may be redesigned in consideration of the codon usage of the microorganism used. The nucleic acid sequences encoding the lysine decarboxylases derived from the above-described organisms are registered in the database (GenBank).

Examples of the promoter sequence, the nucleic acid sequence encoding a secretory signal peptide and the nucleic acid sequence encoding lysine decarboxylase also include nucleic acid sequences which are the same as their respective sequences except that one or several amino acids are substituted, deleted, inserted and/or added, as long as their functions are maintained. The term "several" herein means normally about 1 to 40, preferably about 1 to 30, more preferably about 1 to 20, especially preferably about 1 to 10, most preferably about 1 to 5. Further, examples of the promoter sequence, the nucleic acid sequence encoding a secretory signal peptide and the nucleic acid sequence encoding lysine decarboxylase include nucleic acid sequences that entirely or partially hybridize with those nucleic acid sequences or with the complementary strands thereof under stringent conditions, as long as their functions are maintained. The term "polynucleotide that hybridizes under stringent conditions" herein means a nucleic acid sequence that hybridizes with a probe(s) having one or more nucleic acid sequences each having at least 20, preferably 25, more preferably at least 30 continuous sequences arbitrarily selected from the original base sequence, when a known hybridization technique (Current Protocols I Molecular Biology edit. Ausbel et al., (1987) Publish. John Wily & Sons Section 6.3-6.4) or the like is applied. The stringent conditions herein can be achieved, for example, by performing hybridization in the presence of 50% formamide at a temperature of 37° C., at 42° C. for more stringent conditions, or at 65° C. for even more stringent conditions, followed by washing with 0.1× to 2×SSC solution (composition of ×1 SSC solution: 150 mM sodium chloride, 15 mM sodium citrate). Each of the promoter sequence, the nucleic acid sequence encoding a secretory signal peptide and the nucleic acid sequence encoding lysine decarboxylase may be a nucleic acid sequence having a sequence identity of normally not less than 85%, preferably not less than 90%, more preferably not less than 95% to the original sequence. Each of these promoter sequence, nucleic acid sequence encoding a secretory signal peptide and nucleic acid sequence encoding lysine decarboxylase may be obtained either from an organism other than the original host or by subjecting a nucleic acid sequence obtained from the original host to in vitro mutagenesis or site-directed mutagenesis, which are well-known to those skilled in the art.

In addition to the promoter sequence, nucleic acid sequence encoding a secretory signal peptide and nucleic acid sequence encoding lysine decarboxylase, the gene construct may have a regulatory sequence(s) (operator, terminator and/or the like) necessary for expression of the lysine decarboxylase in the cell of the microorganism at an appropriate position(s) where it/they can function. The vector which can be used for this construct is not restricted as long as the vector can function in the microorganism, and the vector may be one which extrachromosomally and autonomously replicates such as a plasmid, or may be one which is incorporated in the bacterial chromosome. Further, an artificial transposon or the like may also be used. In cases where a transposon is used, the gene of interest is introduced to the chromosome by homologous recombination or by the transposition ability of the transposon itself. Construction and confirmation of the gene construct are carried out according to molecular biological techniques well known to those skilled in the art, and one may refer to, for example, Sambrook et al., Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glovered. 1985); F. M. Ausubel et al. (eds), Current Protocols in Molecular Biology (1994) John Wiley & Sons, Inc.; and PCR Technology: Principles and Application for DNA Amplication, H. Erlich, ed., Stockton Press.

The method of introduction of the gene construct to the microorganism is not restricted, and the gene construct may be introduced by the protoplast method (Gene, (1985), 39, pp. 281-286), electroporation method (Bio/Technology, (1989), 7, 1067-1070) or the like.

The microorganism which extracellularly secretes lysine decarboxylase is preferably a microorganism to which the gene construct can be introduced by genetic recombination, and concrete examples of the microorganism include *E. coli* (*Escherichia coli*), *Bacillus subtilis*, fungi, yeast and coryneform bacteria. Among these, *E. coli* and coryneform bacteria, which are known to efficiently produce lysine, a precursor of cadaverine, are more preferred.

Concrete examples of *E. coli* which may be used include the MC1061 strain, HB101 strain, JM105 strain, JM109 strain, DH5a strain JE5505 strain.

Coryneform bacteria are aerobic gram-positive bacilli, and also include bacteria which had previously been classified in the genus *Brevibacterium* but have now been integrated into the genus *Corynebacterium* (Int. J. Syst., Bacteriol., (1981) 41, p. 225). Coryneform bacteria also include the bacteria belonging to the genus *Brevibacterium*, which is very close to the genus *Corynebacterium*. Examples of such coryneform bacteria include *Corynebacterium acetoacidophylum, Corynebacterium acetoglutamicum, Corynebacterium alkanolyticum, Corynebacterium callunae, Corynebacterium glutamicum, Corynebacterium lilium, Corynebacterium mellassecola, Corynebacterium thermoaminogenes, Corynebacterium efficiens, Corynebacterium herculis, Brevivacterium divaricatum, Brevivacterium flavum, Brevivacterium immariophilum, Brevivacterium lactofermentum, Brevivacterium roseum, Brevivacterium saccharolyticum, Brevivacterium thiogenitalis, Corynebacterium ammoniagenes, Brevivacterium album, Brevivacterium cerinum* and *Microbacterium ammoniaphilum*.

Concrete examples of strains of the respective coryneform bacteria include *Corynebacterium acetoacidophylum* ATCC13870, *Corynebacterium acetoglutamicum* ATCC15806, *Corynebacterium alkanolyticum* ATCC21511, *Corynebacterium callunae* ATCC15991, *Corynebacterium glutamicum* ATCC13020, ATCC13020 and ATCC13060, *Corynebacterium lilium* ATCC15990, *Corynebacterium mellassecola* ATCC17965, *Corynebacterium efficiens* AJ12340 (accession No. FERM BP-1539), *Corynebacterium herculis* ATCC13868, *Brevivacterium divaricatum* ATCC14020, *Brevivacterium flavum* ATCC13826, ATCC14067 and AJ12418 (accession No. FERM BP-2205), *Brevivacterium immariophilum* ATCC14068, *Brevivacterium lactofermentum* ATCC13869, *Brevivacterium roseum* ATCC13825, *Brevivacterium saccharolyticum* ATCC14066, *Brevivacterium thiogenitalis* ATCC19240, *Corynebacterium ammoniagenes* ATCC6871 and ATCC6872, *Brevivacterium album* ATCC15111, *Brevivacterium cerinum* ATCC15112 and *Microbacterium ammoniaphilum* ATCC15354.

The above coryneform bacteria are available from, for example, American Type Culture Collection. That is, a corresponding accession number is given to each strain and described in the catalogue of American Type Culture Collection, and each strain can be obtained by reference to this number.

*Corynebacterium glutamicum* is preferably used among the above-described coryneform bacteria. *Corynebacterium glutamicum* AJ12036 (accession No. FERM BP-734) (originally deposited with International Patent Organism Depositary, National Institute of Advanced Industrial Science and Technology as of Mar. 26, 1984), which was separated as a streptomycin-resistant mutant strain of *Corynebacterium glutamicum* ATCC13869, is assumed to have a mutation in a functional gene involved in secretion of proteins, and its ability of secretory production of foreign proteins is very high and about 2 to 3 times as high as that of the parent strain (wild-type strain) in terms of accumulation of the proteins under the optimal culture conditions. Therefore, *Corynebacterium glutamicum* AJ12036 is suitable as the coryneform bacterium to be made to secrete lysine decarboxylase (see WO02/081694).

Extracellular secretion of lysine decarboxylase by the microorganism that extracellularly secretes lysine decarboxylase can be confirmed by culturing the microorganism and subjecting the resulting culture to centrifugation to separate the microorganism from the culture supernatant, followed by measuring the lysine decarboxylase activity in the obtained culture supernatant to confirm the presence/absence of lysine decarboxylase therein. Further, the amount of lysine decarboxylase in the outside of the cells can be quantified by an assay utilizing antigen-antibody reaction, such as Western blotting or ELISA.

By culturing a microorganism that extracellularly secretes lysine decarboxylase, cadaverine can be produced/accumulated in a culture medium.

Examples of the culture method which may be used include batch culture, fed-batch culture and continuous culture. In cases of continuous culture, continuous culture described in JP 2008-104453 A or the like is preferably carried out.

As a culture medium, a normal nutrient medium comprising a carbon source, nitrogen source, inorganic salt and/or the like may be used. Examples of the carbon source which may be used include saccharides such as glucose, fructose, sucrose, maltose and starch hydrolysates; alcohols such as ethanol; and organic acids such as acetic acid, lactic acid and succinic acid. Examples of the nitrogen source which may be used include ammonia; inorganic and organic ammonium salts such as ammonium chloride, ammonium sulfate, ammonium carbonate and ammonium acetate; nitrogen-containing organic compounds such as urea; and nitrogen-containing organic substances such as meat extracts, yeast extracts, corn steep liquor and soybean hydrolysates. Examples of the inorganic salt which may be used include potassium dihydrogen phosphate, dipotassium hydrogen phosphate, ammonium sulfate, sodium chloride, magnesium sulfate and calcium carbonate. Further, as required, micronutrients such as biotin, thiamine, vitamin B6 and the like may be added. Meat extracts, yeast extracts, corn steep liquor, casamino acids and the like may be used as alternatives to these micronutrients.

Preferably, lysine may be preliminarily added to the culture medium. In cases where lysine is preliminarily added to the culture medium, the preliminarily added lysine is used as a substrate and converted to cadaverine in the culture medium by extracellularly secreted lysine decarboxylase, so that the production efficiency of cadaverine can be enhanced. In the cases where lysine is preliminarily added to the culture medium, the concentration of lysine in the culture medium is not restricted, and the concentration of lysine is preferably one at which the growth of the microorganism is not adversely affected and lysine decarboxylase is not inhibited. More concretely, the concentration is preferably 0.01 to 2 M.

The lysine to be added is preferably L-lysine. The lysine to be added may be either in the free form or a salt of lysine, and the salt of lysine is preferably lysine hydrochloride or a lysine dicarboxylate derived from the dicarboxylic acid described later. Preferred concrete examples of lysine dicarboxylate include lysine adipate, lysine sebacate, lysine 1,12-dodecanedicarboxylate, lysine succinate, lysine isophthalate and lysine terephthalate, and more preferred concrete examples of lysine dicarboxylate include lysine adipate.

The culture conditions are not restricted, and the culture is carried out under aerobic conditions, for example, with shaking or by deep aeration stirring culture. The culture temperature is generally 25° C. to 42° C., preferably 28° C. to 38° C. The culture period is normally 1 day to 6 days.

For adjusting the culture pH, ammonia, hydrochloric acid or dicarboxylic acid is preferably used, and dicarboxylic acid is more preferably used. It is preferred to use the neutralizer to control the culture pH to 5 to 8, more preferably 6.5 to 7.5. The state of the neutralizer is not restricted, and the neutralizer may be used as a gas, liquid, solid or an aqueous solution. The neutralizer is especially preferably an aqueous solution.

The dicarboxylic acid to be preferably used as the neutralizer is not restricted, and the dicarboxylic acid is preferably a dicarboxylic acid having substantially no functional group other than the above-described two carboxylic groups. The functional group herein means a reactive group which reacts, during polyamide polymerization reaction (under reaction conditions wherein, for example, the reaction temperature is 250 to 270° C., the pressure is 10 to 20 kg/cm², and the reaction time is 1 to 5 hour(s)), with an amino group or carboxyl group to cause branching of the polymer or reduction in the degree of crystallinity of the polymer (to a degree of crystallinity of not more than 80%). Examples of the functional group include the amino group and carboxyl group, and other examples of the functional group include acidic groups (e.g., the sulfonic acid group, phosphate group and phenolic hydroxyl group), basic groups (e.g., the hydrazino group), protonic polar groups (e.g., the hydroxyl group), cleavable groups (e.g., the epoxy group and peroxide group) and other highly reactive groups (e.g., isocyanate group). On the other hand, halogen substituents, aromatic substituents, ether groups, ester groups, amide groups and the like are not included in the functional group since their reactivity is low.

The dicarboxylic acid is more preferably a dicarboxylic acid represented by Formula (1), (2) or (3) below.

$$HOOC-(CH_2)_m-COOH \quad (1)$$

(wherein in Formula (1), m=0 to 16).

(2)

(wherein in Formula (2), n, o=0 to 16).

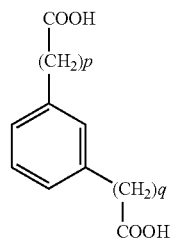
(3)

(wherein in Formula (2), p, q=0 to 16).

The dicarboxylic acid is still more preferably adipic acid, sebacic acid, 1,12-dodecanedicarboxylic acid, succinic acid, isophthalic acid or terephthalic acid.

Cadaverine in the culture medium exists in the free state or as a salt of cadaverine. In the method for collecting cadaverine in the culture medium, the microorganism is first removed from the culture medium. As the method of separation, a conventionally known method such as removal of a microorganism by precipitation, centrifugation, membrane filtration separation or the like is preferably used.

For collecting cadaverine from the culture medium from which the microorganism was removed and which contains cadaverine, cadaverine dicarboxylate may be collected by crystallization as described in JP 2009-207495 A. Alternatively, cadaverine in the free form may be purified and collected using an NF membrane as described in JP 2009-29872 A. Alternatively, cadaverine in the free form may be collected by extraction with a polar organic solvent followed by distillation as described in JP 2009-28045.

EXAMPLES

Our methods will now be described below in detail by way of Examples and Reference Examples. Unless otherwise specified, all media, agar media and culture media used in Examples and Comparative Examples were used after sterilization by a normal sterilization operation (for example, by autoclaving at 121° C. for 30 minutes or sterilization by filtration through a 0.45-µm filter).

(Method of Analysis of Concentrations of Cadaverine and Lysine by HPLC)
Column used: CAPCELL PAK C18 (Shiseido)
Mobile phase: 0.1% (w/w) aqueous phosphate solution:acetonitrile=4.5:5.5
Detection: UV 360 nm
Sample pretreatment: To 25 µl of the sample to be analyzed, 25 µl of 1,4-diaminobutane (0.03 M), 150 µl of sodium hydrogen carbonate (0.075 M) and a solution of 2,4-dinitrofluorobenzene (0.2 M) in ethanol were added, and the resulting mixture was mixed, followed by being incubated at 37° C. for 1 hour. A 50-µl aliquot of the above reaction solution was dissolved in 1 ml of acetonitrile, and resulting the solution was centrifuged at 10,000 rpm for 5 minutes, followed by subjecting 10 µl of the supernatant to HPLC analysis.

Reference Example 1

Preparation of *Corynebacterium glutamicum* Capable of Producing Lysine

To prepare *Corynebacterium glutamicum* capable of synthesizing lysine as a precursor of cadaverine, a lysine-producing bacterium was prepared by introduction of an effective mutation to aspartokinase. By the method described in Apppl.

Microbiol. Biotechnol., (2002), 58, pp. 217-223, the *Corynebacterium glutamicum* AK-1 strain (hereinafter referred to as the AK-1 strain) was prepared. Since, in this bacterial strain, feedback inhibition of aspartokinase by lysine and threonine is relieved, lysine can be synthesized by culture.

Thereafter, the AK-1 strain was subjected to further genetic recombination to prepare coryneform bacteria that extracellularly secrete lysine decarboxylase (Examples 1 and 2) and a coryneform bacterium that does not extracellularly secrete lysine decarboxylase (Comparative Example 1).

Example 1

Preparation of *Corynebacterium glutamicum* which Extracellularly Secretes Lysine Decarboxylase) (Part 1: Use of Tat Pathway)

(1) Cloning of HOM Gene

Homoserine dehydrogenase was selected as the locus to which the lysine decarboxylase gene was to be introduced. The gene corresponding to the region of 300 amino acids from the N-terminus of the HOM gene was cloned. By reference to the base sequence of the HOM gene (Accession No. BA000036) registered in the database (GenBank), oligonucleotide primers (SEQ ID NO:1 and SEQ ID NO:2) were synthesized. In a 0.2-ml microcentrifuge tube, 0.2 μl of a solution of genomic DNA prepared from *Corynebacterium glutamicum* ATCC13032 according to a conventional method as an amplification template was placed, and each reagent was added to the tube such that the resulting mixture, in a total volume of 50 μl, contained 20 pmol each primer, Tris-HCl buffer pH 8.0 (20 mM), potassium chloride (2.5 mM), gelatin (100 μg/ml), each dNTP (50 μM) and LA Taq DNA polymerase (2 units) (manufactured by Takara Shuzo Co., Ltd.). Polymerase chain reaction (hereinafter referred to as PCR) was carried out using a thermal cycler manufactured by Bio-Rad under the conditions of 30 cycles of: denaturation of DNA at 94° C. for 30 seconds, annealing of the primers at 55° C. for 30 seconds, and extension reaction of the DNA primers at 72° C. for 3 minutes. The PCRs in the present Examples were carried out under the above conditions unless otherwise specified. The product obtained by this PCR was subjected to electrophoresis in 1% agarose, and a DNA fragment of about 0.9 kb containing the HOM gene was excised from the gel, followed by being purified using the GENECLEAN kit (manufactured by BIO 101). This fragment was digested with the restriction enzymes EcoRI and BamHI, and the obtained 0.9-kb EcoRI-BamHI fragment was inserted into the EcoRI/BamHI gap of pHSG298 (manufactured by Takara Shuzo Co., Ltd.) which had been preliminarily digested with EcoRI and BamHI, using the Ligation kit Ver. 1 (manufactured by Takara Shuzo Co., Ltd.). The obtained plasmid was designated pHOM1.

(2) Preparation of LDC Secretory Expression Cassette

The promoter of the kanamycin-resistant gene was selected as a promoter for constitutional expression of LDC in *Corynebacterium glutamicum*; Sufi of *E. coli*, whose secretion is dependent on the Tat pathway, was selected as a secretion signal; and cadA of *E. coli* was selected as the LDC gene.

First, the promoter of the kanamycin-resistant gene was cloned. By reference to the base sequence of pHSG299 (Accession No. M19415) registered in the database (GenBank), oligonucleotide primers (SEQ ID NO:3 and SEQ ID NO:4) were synthesized. Using the plasmid pHSG299 as an amplification template and the oligonucleotides (SEQ ID NO:3) (SEQ ID NO:4) as a primer set, PCR was carried out to obtain a product, which was then subjected to electrophoresis in 1% agarose gel. A DNA fragment of 0.3 kb containing the promoter region of the kanamycin-resistant gene was excised from the gel, and was purified using the GENECLEAN kit. This fragment was inserted into the gap in the plasmid vector pT7blue (manufactured by Novagen) using the Ligation kit Ver. 1, which gap had been prepared by digesting the vector with EcoRV and adding the base T to the 3' termini. Among the obtained plasmids, the plasmid which became a single fragment of 3.2 kb after digestion with HindIII and SacII was designated pKMP1.

Thereafter, the LDC gene was cloned. By reference to the base sequence of the LDC gene (Accession No. M76411) registered in the database (GenBank), oligonucleotide primers (SEQ ID NO:5 and SEQ ID NO:6) were synthesized. Using a solution of genomic DNA prepared from *E. coli* (*Escherichia coli* ATCC10798) according to a conventional method as an amplification template and the oligonucleotides (SEQ ID NOs:5 and 6) as a primer set, PCR was carried out to obtain a product, which was then subjected to electrophoresis in 1% agarose gel. A DNA fragment of 2.1 kb containing the LDC gene was excised from the gel, and was purified using the GENECLEAN kit. This fragment was inserted into the gap in the plasmid vector pT7blue using the Ligation kit Ver. 1, which gap had been prepared by digesting the vector with EcoRV and adding the base T to the 3' termini. Among the obtained plasmids, the plasmid which became a single fragment of 4.0 kb after digestion with HindIII and NcoI was designated pCADA.

Finally, an oligonucleotide primer (SEQ ID NO:7) wherein a base sequence corresponding to the amino acid sequence of SufI of *E. coli* as a secretion signal is fused to the LCD gene was synthesized. This oligonucleotide primer was designed such that its 3' side has a region which overlaps with the 5' side of the LDC gene. Using pCADA as an amplification template and the oligonucleotides (SEQ ID NOs:7 and 6) as a primer set, PCR was carried out to obtain a product, which was then subjected to electrophoresis in 1% agarose gel. A DNA fragment of 2.2 kb containing the LDC gene was excised from the gel, and was purified using the GENECLEAN kit (LDC gene fragment 1). Further, an oligonucleotide primer (SEQ ID NO:8) wherein a base sequence corresponding to the amino acid sequence of SufI of *E. coli* as a secretion signal is fused to the promoter of the kanamycin-resistant gene was synthesized. This oligonucleotide primer was designed such that its 5' side has a region which overlaps with the 3' side of the promoter of the kanamycin-resistant gene. Using pKMP1 as an amplification template and the oligonucleotides (SEQ ID NOs:3 and 8) as a primer set, PCR was carried out to obtain a product, which was then subjected to electrophoresis in 1% agarose gel. A DNA fragment of 0.4 kb containing the LDC gene was excised from the gel, and was purified using the GENECLEAN kit (kanamycin-resistant-gene promoter fragment 1).

Using the thus obtained LDC gene fragment 1 and the kanamycin-resistant-gene promoter fragment 1 as amplification templates, and an oligonucleotide primer designed to contain the recognition sequence for the restriction enzyme BamHI (SEQ ID NO:9) and an oligonucleotide primer designed to contain the recognition sequence for the restriction enzyme SphI (SEQ ID NO:10) as a primer set, PCR was carried out to obtain a product, which was then subjected to electrophoresis in 1% agarose gel. A DNA fragment of 2.6 kb containing the LDC secretory expression cassette was excised from the gel, and was purified using the GENECLEAN kit. This fragment was digested with the restriction enzymes BamHI and SphI, and the resulting BamHI-SphI fragment of 2.6 kb was inserted into the BamHI- SphI gap of pHOM1 which had been preliminarily digested with BamHI and SphI, using the Ligation kit Ver. 1 (manufactured by Takara Shuzo Co., Ltd.). The obtained plasmid was designated pTM65.

(4) Incorporation of pTM65 into Chromosome

The plasmid pTM65 was introduced to the AK-1 strain by electroporation [FEMS Microbiology Letters, 65, p. 299 (1989)], and subjected to selection on LB agar medium (tryptone (10 g/l) (manufactured by Bacto), yeast extract (5 g/l) (manufactured by Bacto), sodium chloride (10 g/l)) supplemented with kanamycin (25 µg/ml). From the thus selected transformant, a genomic DNA solution was prepared according to a conventional method. Using this genomic DNA as a template and the oligonucleotides (SEQ ID NO:1) (SEQ ID NO:6) as a primer set, PCR was carried out to obtain a product, which was then subjected to electrophoresis in 1.0% agarose. As a result, a single band of 3.5 kb was observed. By this, it could be confirmed that the selected transformant has the LDC gene inserted at the HOM locus. This transformant was designated *Corynebacterium glutamicum* AK-1/pTM65 (hereinafter referred to as the AK-1/pTM65 strain for short).

Example 2

Preparation of *Corynebacterium glutamicum* which Extracellularly Secretes Lysine Decarboxylase) (Part 1: Via Sec Pathway)

(1) Preparation of LDC Secretory Expression Cassette

Subsequently, the promoter of the kanamycin-resistant gene was selected as a promoter for constitutional expression of LDC in *Corynebacterium glutamicum*; arpE, which is the signal for secretion of subtilisin via the Sec pathway was selected as a secretion signal; and cadA of *E. coli* was selected as the LDC gene. Similarly to Example 1, an oligonucleotide primer (SEQ ID NO:11) wherein a base sequence corresponding to the amino acid sequence of arpE as a secretion signal is fused to the LCD gene was synthesized. This oligonucleotide primer was designed such that its 3' side has a region which overlaps with the 5' side of the LDC gene. Using pCADA as an amplification template and the oligonucleotides (SEQ ID NO:11 and SEQ ID NO:6) as a primer set, PCR was carried out to obtain a product, which was then subjected to electrophoresis in 1% agarose gel. A DNA fragment of 2.2 kb containing the LDC gene was excised from the gel, and was purified using the GENECLEAN kit (LDC gene fragment 2).

Further, an oligonucleotide primer (SEQ ID NO:12) wherein a base sequence corresponding to the amino acid sequence of arpE as a secretion signal is fused to the promoter of the kanamycin-resistant gene was synthesized. This oligonucleotide primer was designed such that its 5' side has a region which overlaps with the 3' side of the kanamycin-resistant-gene promoter. Using pKMP1 as an amplification template and the oligonucleotides (SEQ ID NO:3 and SEQ ID NO:12) as a primer set, PCR was carried out to obtain a product, which was then subjected to electrophoresis in 1% agarose gel. A DNA fragment of 0.4 kb containing the LDC gene was excised from the gel, and was purified using the GENECLEAN kit (kanamycin-resistant-gene promoter fragment 2).

Using the thus obtained LDC gene fragment 2 and the kanamycin-resistant-gene promoter fragment 2 as amplification templates, and the oligonucleotide primers (SEQ ID NO:9) and (SEQ ID NO:10) as a primer set, PCR was carried out to obtain a product, which was then subjected to electrophoresis in 1% agarose gel. A DNA fragment of 2.6 kb containing the LDC secretory expression cassette was excised from the gel, and was purified using the GENECLEAN kit. This fragment was digested with the restriction enzymes BamHI and SphI, and the resulting BamHI-SphI fragment of 2.6 kb was inserted into the BamHI-SphI gap of pHOM1 which had been preliminarily digested with BamHI and SphI, using the Ligation kit Ver. 1 (manufactured by Takara Shuzo Co., Ltd.). The obtained plasmid was designated pTM66.

(2) Incorporation of pTM66 into Chromosome

The plasmid pTM66 was introduced to the AK-1 strain by electroporation [FEMS Microbiology Letters, 65, p. 299 (1989)], and subjected to selection on LB agar medium (tryptone (10 g/l) (manufactured by Bacto), yeast extract (5 g/l) (manufactured by Bacto), sodium chloride (10 g/l)) supplemented with kanamycin (25 µg/ml). From the thus selected transformant, a genomic DNA solution was prepared according to a conventional method. Using this genomic DNA as a template and the oligonucleotides (SEQ ID NO:1 and SEQ ID NO:6) as a primer set, PCR was carried out to obtain a product, which was then subjected to electrophoresis in 1.0% agarose. As a result, a single band of 3.5 kb was observed. By this, it could be confirmed that the selected transformant has the LDC gene inserted at the HOM locus. This transformant was designated *Corynebacterium glutamicum* AK-1/pTM66 (hereinafter referred to as the AK-1/pTM66 strain for short).

Comparative Example 1

Preparation of *Corynebacterium glutamicum* which does not Extracellularly Secrete Lysine Decarboxylase pKMP1 was digested with HindIII and NcoI, and the resulting product was subjected to electrophoresis in 1.2% agarose. A DNA fragment of 0.3 kb containing the promoter region of the kanamycin resistant gene was excised from the gel, and was purified using the GENECLEAN kit. The thus obtained HindIII-NcoI fragment was inserted into the HindIII/NcoI gap of pCADA which had been preliminarily digested with HindIII and NcoI, using the Ligation kit Ver. 1. The obtained plasmid was designated pTM100.

Thereafter, pTM100 was digested with SacII, and the resulting product was subjected to electrophoresis in 1.0% agarose gel. A DNA fragment of 2.4 kb containing the LDC expression cassette was excised from the gel, and was purified using the GENECLEAN kit. The thus obtained SacII fragment was inserted into the SacII gap of pHOM1 which had been preliminarily digested with SacII, using the Ligation kit Ver. 1. The obtained plasmid was designated pTM101.

The plasmid pTM101 was introduced to the AK-1 strain by electroporation [FEMS Microbiology Letters, 65, p. 299 (1989)], and subjected to selection on LB agar medium (tryptone (10 g/l) (manufactured by Bacto), yeast extract (5 g/l) (manufactured by Bacto), sodium chloride (10 g/l)) supplemented with kanamycin (25 µg/ml).

From the thus selected transformant, a genomic DNA solution was prepared according to a conventional method. Using this genomic DNA as a template and the oligonucleotides (SEQ ID NO:5) (SEQ ID NO:6) as a primer set, PCR was carried out to obtain a product, which was then subjected to electrophoresis in 1.0% agarose. As a result, a single band of 2.1 kb was observed. By this, it could be confirmed that the selected transformant has the LDC gene inserted at the HOM locus. This transformant was designated *Corynebacterium*

*glutamicum* AK-1/pTM101 (hereinafter referred to as the AK-1/pTM101 strain for short).

Example 3

Confirmation of Extracellular Secretion of Lysine Decarboxylase Activity

Each of the AK-1/pTM65 strain, AK-1/pTM66 strain and AK-1/pTM101 strain was cultured in BY medium (see J. Bacteriol., 159, pp. 306-311 (1984)), and the obtained culture was separated into the microorganism and the culture supernatant by centrifugation. The microorganism was homogenized according to a conventional method, to prepare a microorganism homogenate. The lysine decarboxylase activities in the thus obtained culture supernatant and microorganism homogenate were measured (see Biosci. Biotechnol. Biochem., 71, pp. 2130-2135, (2007)). Taking the enzyme activity with which L-lysine is converted to 1 nmol of cadaverine in 1 minute as 1 U, the results are shown in Table 1 in terms of the specific activity per protein weight.

TABLE 1

| Microorganism name | Lysine decarboxylase activity [mU/mg] | |
| --- | --- | --- |
| | Microorganism homogenate | Culture supernatant |
| AK-1/pTM101 strain | 19800 | 0 |
| AK-1/pTM65 strain | 44900 | 340 |
| AK-1/pTM66 strain | 57100 | 550 |

Since the AK-1/pTM65 strain and AK-1/pTM66 strain had lysine decarboxylase activity in the culture supernatant, that is, in the outside of the cells, it could be confirmed that lysine decarboxylase was extracellularly secreted in these cases. Further, it could be confirmed that all the strains had lysine decarboxylase activity in the microorganism homogenate.

Examples 4 and 5, and Comparative Examples 2 and 3

Microorganism Culture: Cases where Microorganism is Coryneform Bacterium

The AK-1/pTM65 strain (Example 4), AK-1/pTM66 strain (Example 5), AK-1/pTM101 strain (Comparative Example 2) and AK-1/pTM101 strain+20 mg purified lysine decarboxylase (prepared by the method described in JP 2004-000114 A) (Comparative Example 3) were cultured, and these were compared for the cadaverine productivity.

Into 5 ml of sterilized BY medium, one platinum loop of each strain was inoculated, and pre-preculture was carried out at 30° C. for 24 hours with shaking. The entire volume of the obtained pre-preculture was inoculated into 50 ml of the same medium as in the pre-preculture, and preculture was carried out at 30° C. with a shaking amplitude of 30 cm at 120 rpm for 24 hours. Thereafter, the entire volume of the obtained pre-culture was inoculated into 950 ml of MMP medium (culture medium) shown in Table 2, and culture was carried out under aeration with sterilized air at 0.07 vvm at 30° C. at a stirring blade rotation speed of 800 rpm at a controlled pH of 6.7 for 50 hours. As neutralizers, an aqueous sulfuric acid solution (3 M) and aqueous ammonia (3 M) were used. In Comparative Example 3, 20 mg of purified lysine decarboxylase was added at the beginning of the culture.

TABLE 2

| Medium components | Final concentration [g/L] |
| --- | --- |
| Glucose | 50 |
| $(NH_4)_2SO_4$ | 20 |
| Bacto Peptone | 5 |
| $KH_2PO_4$ | 2.5 |
| $K_2HPO_4$ | 2.75 |
| NaCl | 0.5 |
| $MgSO_4 \cdot 7H_2O$ | 0.75 |
| $CaCl_2 \cdot 2H_2O$ | 0.05 |
| $FeSO_4 \cdot 7H_2O$ | 0.01 |
| $MnSO_4 \cdot 4$~$6H_2O$ | 0.001 |
| Biotin | 0.0005 |
| Tiamine•HCl | 0.007 |
| L-homoserine | 0.5 |

After completion of the culture, the microorganism was removed by centrifugation at 4° C. at 8,000 rpm for 10 minutes, followed by recovering the culture supernatant. Cadaverine and lysine in this culture supernatant were analyzed by HPLC. For measuring the glucose concentration, "GULCOSE TEST WAKO" (registered trademark) (manufactured by Wako Pure Chemical Industries, Ltd.) was used. The yield of cadaverine relative to glucose consumption ((weight of cadaverine produced/weight of glucose consumed)×100(%)) was calculated. The results are shown in Table 3.

TABLE 3

| | Comparative Example 2 AK-1/ pTM101 | Comparative Example 3 AK-1/ pTM101 + Lysine decarboxylase | Example 4 AK-1/ pTM65 (via Tat pathway) | Example 5 AK-1/ pTM66 (via Sec pathway) |
| --- | --- | --- | --- | --- |
| Cadaverine [g/L] | 5.6 | 6.4 | 7.5 | 7.1 |
| Lysine [g/L] | 1.2 | 0.0 | 0.0 | 0.0 |
| Yield of cadaverine relative to glucose consumption [%] | 11.2 | 12.8 | 15.0 | 14.2 |

As a result, in Comparative Examples 2 and 3, an effect that allows assumption that by-production of lysine can be reduced by addition of lysine decarboxylase to the outside of the cells was observed. On the other hand, by comparison between Comparative Example 2 and Examples 4 and 5, it was revealed that by-production of lysine can be remarkably reduced by allowing extracellular secretion of lysine decarboxylase. Surprisingly, although it had been expected that the increase in the concentration of accumulated cadaverine and the increase in the yield of cadaverine relative to glucose consumption are not different between Comparative Example 3 and Examples 4 and 5, it could be confirmed that culturing a microorganism that extracellularly secretes lysine decarboxylase results in larger increases in the concentration of accumulated cadaverine and the yield of cadaverine relative to glucose consumption, as compared to cases where lysine decarboxylase is added to the culture medium.

Reference Example 2

Preparation of *E. coli* Deficient for Lysine Decarboxylase (1) Deletion of Lysine Decarboxylase (LDC) Gene in *E. coli*
It is known that *E. coli* has the cadA gene and the ldcC gene as LDC genes. According to the method called "Red-driven

*integration"*, which was developed by Datsenko and Wanner (Proc. Natl. Acad. Sci. USA, 2000, vol. 97, No. 12, pp. 6640-6645), the cadA and ldcC genes in the *E. coli* W3110 strain were deleted as follows. In the "Red-driven integration" method, synthetic oligonucleotides each of which was designed such that its 5' side has a part of the gene of interest and its 3' side has a part of an antibiotic resistance gene are used as primers to obtain a PCR product, which can then be used for one-step construction of a gene-deficient strain. Further, using FLP recombinase derived from yeast, the antibiotic resistance gene that was incorporated into the gene-deficient strain can be removed.

(1-1) Deletion of cadA Gene

As a template for PCR, the plasmid pKD3 (Proc. Natl. Acad. Sci. USA, 2000, vol. 97, No. 12, pp. 6640-6645) was used. pKD3 is a plasmid produced by inserting FRT (FLP recombinase Recognition Target), which is the recognition sequence of FLP-recombinase, and the cat gene, which is an antibiotic resistance gene, to pMW118 (manufactured by Takara Bio Inc.). These are inserted in the order of FRT-cat-FRT. FRT is shown in SEQ ID NO:75.

PCR was carried out using as primers the synthetic oligonucleotides shown in SEQ ID NOs: 76 and 77, whose 3' ends have sequences corresponding to the both ends of the FRT and whose 5' ends each have 50 bases flanking the open reading frame (ORF) of the cadA gene.

The amplified PCR product was purified through agarose gel, and introduced by electroporation to the *E. coli* W3110 strain carrying pKD46, which is a plasmid having temperature-sensitive replication capacity. The plasmid pKD46 (Proc. Natl. Acad. Sci. USA, 2000, vol. 97, No. 12, pp. 6640-6645) comprises a DNA fragment of λ phage having a total length of 2154 bases (GenBank/EMBL accession No. J02459, positions 31088 to 33241) comprising the genes encoding Red recombinase (γ, β and exo genes) for the λ Red homologous recombination system regulated by the arabinose-inducible ParaB promoter.

Competent cells for the electroporation were prepared as follows. That is, the *E. coli* W3110 strain was cultured in LB medium supplemented with ampicillin at 30° C. overnight, and the obtained culture was then 100-fold diluted with SOB medium supplemented with ampicillin and L-arabinose. The obtained diluted cells were allowed to grow at 30° C. under aeration until OD600 reaches about 0.6, and were washed 3 times with 10% glycerol, so that the cells could be used in electroporation.

To the cells after the electroporation, 1 mL of SOC medium was added, and the cells were then cultured at 37° C. for 2.5 hours. Subsequently, the cells were subjected to plate culture at 37° C. on LB agar medium supplemented with chloramphenicol, by which a chloramphenicol-resistant recombinant was selected. Thereafter, for removing the pKD46 plasmid, the cells were subcultured twice at 42° C. on LB agar medium supplemented with chloramphenicol. The obtained colonies were tested for ampicillin resistance, and an ampicillin-sensitive strain, in which pKD46 is lost, was obtained.

Loss of the cadA gene in the mutant which could be identified with the chloramphenicol-resistant gene was confirmed by PCR. The obtained cadA-deficient strain was designated the W3110 cadA::FRT-cat-FRT strain.

Thereafter, to remove the FRT-cat-FRT gene introduced into the cadA gene, the helper plasmid pCP20 was used. pCP20 (Proc. Natl. Acad. Sci. USA, 2000, vol. 97, No. 12, pp. 6640-6645) is a plasmid which carries yeast FLP recombinase and has temperature-sensitive replication capacity. By introduction of pCP20, the recombinase recognizes FRT at two sites in the chromosome to cause recombination, thereby cleaving out the gene between the FRT sites, finally leaving only FRT in the chromosome.

Competent cells of the thus obtained W3110 cadA::FRT-cat-FRT strain were prepared according to a conventional method, and transformed with the helper plasmid pCP20. The cells were then subjected to plate culture at 30° C. on LB agar medium supplemented with 50 mg/L ampicillin, by which an ampicillin-resistant strain was selected. Thereafter, for removing pCP20, the cells were subcultured twice at 42° C. on LB agar medium. The obtained colonies were tested for ampicillin resistance and chloramphenicol resistance, and a chloramphenicol/ampicillin-sensitive strain, in which the cat gene and pCP20 are lost, was obtained. This strain was designated W3110 ΔcadA.

(1-2) Deletion of ldcC Gene

Deletion of the ldcC gene in the *E. coli* W3110 ΔcadA strain was carried out according to the method in the above (1-1) using the primers shown in SEQ ID NOs: 78 and 79 as primers for destroying ldcC. By this, a strain in which the cadA and ldcC genes were deleted was obtained. The constructed bacterial strain was designated W3110 ΔLDC.

Examples 6 and 7, Comparative Example 4

Preparation of *E. coli* Strains which Extracellularly Secrete Lysine Decarboxylase (Via Sec Pathway and Via Tat Pathway) and Preparation of *E. coli* Strain which does not Extracellularly Secrete Lysine Decarboxylase The W3110 ΔLDC strain was transformed with the plasmids pTM101, pTM65 and pTM66 according to a conventional method. The recombinant *E. coli* strains were designated the W3110 ΔLDC/pTM101 strain (strain without extracellular secretion) (Comparative Example 4), W3110 ΔLDC/pTM65 strain (strain with extracellular secretion: via the Tat pathway) (Example 6) and W3110 ΔLDC/pTM66 strain (strain with extracellular secretion: via the Sec pathway) (Example 7), respectively.

Example 8

Confirmation of Extracellular Secretion of Lysine Decarboxylase

The W3110 ΔLDC/pTM101 strain, W3110 ΔLDC/pTM65 strain and W3110 ΔLDC/pTM66 strain were cultured in LB medium supplemented with kanamycin, and each obtained culture was separated into the microorganism and the culture supernatant by centrifugation. The microorganism was homogenized according to a conventional method, to prepare a microorganism homogenate. The lysine decarboxylase activities in the thus obtained culture supernatant and microorganism homogenate were measured. Taking the enzyme activity with which L-lysine is converted to 1 nmol of cadaverine in 1 minute as 1 U, the results are shown in Table 4 in terms of the specific activity per protein weight.

TABLE 4

| | LDC activity [mU/mg] | |
|---|---|---|
| Microorganism name | Microorganism homogenate | Culture supernatant |
| W3110 ΔLDC/pTM101 strain | $15700 \times 10^3$ | 0 |
| W3110 ΔLDC/pTM65 strain | $18700 \times 10^3$ | $10 \times 10^3$ |
| W3110 ΔLDC/pTM66 strain | $19700 \times 10^3$ | $12 \times 10^3$ |

In the cases of the W3110 ΔLDC/pTM101 strain and W3110 ΔLDC/pTM65 strain, since the culture supernatant, which is the outside of the cells, had lysine decarboxylase activity, it could be confirmed that lysine decarboxylase was extracellularly secreted. Further, all the strains could be confirmed to have lysine decarboxylase in the their microorganism homogenates.

Examples 9 and 10, Comparative Example 5

Microorganism Culture: Cases where Microorganism is *E. coli*

The W3110 ΔLDC/pTM65 strain (Example 9), W3110 ΔLDC/pTM66 strain (Example 10) and W3110 ΔLDC/pTM101 strain+20 m purified lysine decarboxylase (prepared by the method described in JP 2004-000114 A) (Comparative Example 5) were cultured, and these were compared for the cadaverine productivity.

Into 5 ml of LB medium supplemented with kanamycin, one platinum loop of each strain was inoculated, and pre-preculture was carried out at 30° C. for 24 hours with shaking. The entire volume of the obtained pre-preculture was inoculated into 50 ml of the same medium as in the pre-preculture, and preculture was carried out at 30° C. with a shaking amplitude of 30 cm at 120 rpm for 24 hours. Thereafter, the entire volume of the obtained preculture was inoculated into 950 ml of MS medium (culture medium) shown in Table 5, and culture was carried out under aeration with sterilized air at 0.20 vvm at 37° C. at a stirring blade rotation speed of 800 rpm at a controlled pH of 7.0 for 50 hours. As neutralizers, an aqueous sulfuric acid solution (3 M) and aqueous ammonia (3 M) were used. In Comparative Example 6, 20 mg of purified lysine decarboxylase was added at the beginning of the culture.

TABLE 5

| Medium components | Final concentration [g/L] |
|---|---|
| Glucose | 40 |
| (NH$_4$)$_2$SO$_4$ | 16 |
| Polypeptone S | 10 |
| KH$_2$PO$_4$ | 1 |
| MgSO$_4$•7H$_2$O | 1 |
| FeSO$_2$•7H$_2$O | 0.01 |
| MnSO$_4$•5H$_2$O | 0.01 |

After completion of the culture, the microorganism was removed by centrifugation at 4° C. at 8,000 rpm for 10 minutes, followed by recovering the culture supernatant. Cadaverine and lysine in this culture supernatant were analyzed by HPLC. For measuring the glucose concentration, "GULCOSE TEST WAKO" (registered trademark) (manufactured by Wako Pure Chemical Industries, Ltd.) was used. The yield of cadaverine relative to glucose consumption ((weight of cadaverine produced/weight of glucose consumed)×100(%)) was calculated. The results are shown in Table 6.

TABLE 6

| | Comparative Example 5 W3110 ΔLDC/pTM101 + Lysine decarboxylase | Example 9 W3110 ΔLDC/pTM65 (via Tat pathway) | Example 10 W3110 ΔLDC/pTM66 (via Sec pathway) |
|---|---|---|---|
| Cadaverine [g/L] | 0.57 | 1.52 | 1.72 |
| Lysine [g/L] | 0 | 0 | 0 |
| Yield of cadaverine relative to glucose consumption [%] | 1.42 | 3.86 | 4.3 |

Based on comparison between Comparative Example 5 and Examples 9 and 10, it could be surprisingly confirmed that culturing a microorganism that extracellularly secretes lysine decarboxylase results in larger increases in the concentration of accumulated cadaverine and the yield of cadaverine relative to glucose consumption, as compared to cases where lysine decarboxylase is added to the culture medium.

Examples 11 and 12, Comparative Examples 6 and 7

Microorganism Culture: Comparison of Effect of Addition of Lysine

The W3110 ΔLDC/pTM65 strain (Example 11), W3110 ΔLDC/pTM66 strain (Example 12), W3110 ΔLDC/pTM101 strain (Comparative Example 6) and W3110 ΔLDC/pTM101 strain+20 mg purified lysine decarboxylase (prepared by the method described in JP 2004-000114 A) (Comparative Example 7) were subjected to comparison of the ability to convert lysine into cadaverine. Each microorganism was cultured in the same manner as in Examples 9 and 10 except that 62.5 g/L L-lysine hydrochloride was added to MS medium (culture medium). After 50 hours of the culture, the microorganism was removed by centrifugation at 4° C. at 8,000 rpm for 10 minutes, and the culture supernatant was recovered. Cadaverine and lysine in this culture supernatant were analyzed by HPLC. The results are shown in Table 7.

TABLE 7

| | Comparative Example 6 W3110 ΔLDC/ pTM101 | Comparative Example 7 W3110 ΔLDC/ pTM101 + Lysine decarboxylase | Example 11 W3110 ΔLDC/ pTM65 (via Tat pathway) | Example 12 W3110 ΔLDC/ pTM66 (via Sec pathway) |
|---|---|---|---|---|
| Cadaverine [g/L] | 5.78 | 21.2 | 29.5 | 29.5 |
| Lysine [g/L] | 40.6 | 8.2 | 0 | 0 |
| Cadaverine production rate [g/L · h] | 0.12 | 0.42 | 0.59 | 0.59 |

Based on comparison between Comparative Examples 6 and 7 and Examples 11 and 12, it could be confirmed that the cadaverine production efficiency (production rate) is remarkably higher in the organisms that extracellularly secrete lysine decarboxylase. By this, it was revealed that addition of lysine upon culture of a microorganism that extracellularly secretes lysine decarboxylase improves the production efficiency of cadaverine.

Examples 13 and 14, Comparative Example 8

Microorganism Culture: Comparison with Microorganism Having Lysine Decarboxylase Bound to its Surface Microorganisms that extracellularly secrete lysine decarboxylase (hereinafter referred to as LDC-secreting microorganisms) and the JM109/pTM16 strain described in JP 2004-298033 A as a microorganism having lysine decarboxylase on its surface (hereinafter referred to as an LDC-cell-surface-presenting microorganism) were cultured, and these were compared for the cadaverine productivity.

One platinum loop of each of the W3110 ΔLDC/pTM65 strain (Example 13), W3110 ΔLDC/pTM66 strain (Example 14), and JCM109/pTM16 strain (Comparative Example 8) was inoculated into 5 ml of LB medium supplemented with kanamycin (LB medium supplemented with ampicillin in the case of the JCM109/pTM16 strain), and pre-preculture was carried out at 30° C. for 24 hours with shaking. The entire volume of the obtained pre-preculture was inoculated into 50 ml of the same medium as in the pre-preculture, and preculture was carried out at 30° C. with a shaking amplitude of 30 cm at 120 rpm for 24 hours. Thereafter, the entire volume of the obtained preculture was inoculated into 950 ml of MS medium (culture medium) supplemented with isopropyl-thio-β-D-galactoside at a final concentration of 1 mM, and culture was carried out under aeration with sterilized air at 0.20 vvm at 37° C. at a stirring blade rotation speed of 800 rpm at a controlled pH of 7.0 for 50 hours. As neutralizers, an aqueous sulfuric acid solution (3 M) and aqueous ammonia (3 M) were used.

After completion of the culture, the microorganism was removed by centrifugation at 4° C. at 8,000 rpm for 10 minutes, followed by recovering the culture supernatant. Cadaverine and lysine in this culture supernatant were analyzed by HPLC. For measuring the glucose concentration, "GULCOSE TEST WAKO" (registered trademark) (manufactured by Wako Pure Chemical Industries, Ltd.) was used. The yield of cadaverine relative to glucose consumption ((weight of cadaverine produced/weight of glucose consumed)×100(%)) was calculated. The results are shown in Table 8.

TABLE 8

| | Comparative Example 8 JCM109/pTM16 (Cell-surface presentation) | Example 13 W3110 ΔLDC/pTM65 (via Tat pathway) | Example 14 W3110 ΔLDC/pTM66 (via Sec pathway) |
|---|---|---|---|
| Cadaverine [g/L] | 0.24 | 1.35 | 1.41 |
| Lysine [g/L] | 0.15 | 0 | 0 |
| Yield of cadaverine relative to glucose consumption [%] | 0.6 | 3.38 | 3.53 |

Based on comparison between Comparative Example 8 and Examples 13 and 14, it could be surprisingly confirmed that culturing an LDC-secreting microorganism results in larger increases in the concentration of accumulated cadaverine and the yield of cadaverine relative to glucose consumption, as compared to cases where an LDC-cell-surface-presenting microorganism is cultured.

INDUSTRIAL APPLICABILITY

Our methods can be suitably applied to production of cadaverine.

The invention claimed is:

1. A method of producing cadaverine comprising:
   culturing a transformed microorganism with a gene encoding lysine decarboxylase that extracellularly secretes lysine decarboxylase to increase yield of cadaverine relative to glucose consumption, wherein the microorganism is selected from the group consisting of *Corynebacterium glutamicum* and *E. coli*,
   the microorganism intracellularly expresses a protein comprising lysine decarboxylase having a secretory signal peptide attached to the N-terminus side of the amino acid sequence thereof, which lysine decarboxylase is thereby extracellularly secreted, and
   the secretory signal peptide is a peptide represented by the amino acid sequence shown in any of SEQ ID NOs: 13 to 43 or a peptide having a sequence identity of not less than 85% to the amino sequence shown in any of SEQ ID NOs: 13 to 43.

2. The method according to claim 1, wherein lysine is added to a medium to culture said microorganism.

3. The method according to claim 1, wherein said lysine decarboxylase is obtained from *E. coli*.

4. The method according to claim 1, wherein said microorganism has a gene construct comprising, in a direction from 5' to 3' of the nucleic acid sequence, a promoter sequence that functions in the microorganism, a nucleic acid sequence encoding said secretory signal peptide and a nucleic acid sequence encoding lysine decarboxylase, which gene construct allows intracellular expression of said protein comprising lysine decarboxylase having said secretory signal peptide attached to the N-terminus side of the amino acid sequence thereof.

5. The method according to claim 2, wherein said lysine decarboxylase is obtained from *E. coli*.

6. The method according to claim 1, wherein said lysine decarboxylase is obtained from *E. coli*.

7. The method according to claim 1, wherein the sequence identity is not less than 90%.

8. The method according to claim 1, wherein the sequence identity is not less than 95%.

9. A method of producing cadaverine comprising:
culturing a transformed microorganism with a gene encoding lysine decarboxylase that extracellularly secretes lysine decarboxylase to increase yield of cadaverine relative to glucose consumption, wherein the microorganism is selected from the group consisting of *Corynebacterium glutamicum* and *E. coli*,
the microorganism intracellularly expresses a protein comprising lysine decarboxylase having a secretory signal peptide attached to the N-terminus side of the amino acid sequence thereof, which lysine decarboxylase is thereby extracellularly secreted,
the secretory signal peptide is a peptide represented by the amino acid sequence shown in any of SEQ ID NOs: 13 to 43 or a peptide having a sequence identity of not less than 85% to the amino sequence shown in any of SEQ ID NOs: 13 to 43, and
the microorganism has a gene construct comprising, in a direction from 5' to 3' of the nucleic acid sequence, a promoter sequence that functions in the microorganism, a nucleic acid sequence encoding said secretory signal peptide and a nucleic acid sequence encoding lysine decarboxylase, which gene construct allows intracellular expression of said protein comprising lysine decarboxylase having said secretory signal peptide attached to the N-terminus side of the amino acid sequence.

10. The method according to claim 9, wherein the sequence identity is not less than 90%.

11. The method according to claim 9, wherein the sequence identity is not less than 95%.

* * * * *

```
SEQUENCE LISTING

<160> NUMBER OF SEQ ID NOS: 79

<210> SEQ ID NO 1
<211> LENGTH: 29
<212> TYPE: DNA
<213> ORGANISM: Corynebacterium glutamicum

<400> SEQUENCE: 1
gaagaattct aaacctcagc atctgcccc                                       29

<210> SEQ ID NO 2
<211> LENGTH: 30
<212> TYPE: DNA
<213> ORGANISM: Corynebacterium glutamicum

<400> SEQUENCE: 2
gaaggatcca aaggacttgt ttaccgacgc                                      30

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      plasmid pHSG299 oligonucleotide

<400> SEQUENCE: 3
gaaccgcggc ctgaatcgcc ccatcatcc                                       29
```

```
<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      plasmid pHSG299 oligonucleotide

<400> SEQUENCE: 4
gaaccatggc cccttgtatt actg                                            24

<210> SEQ ID NO 5
<211> LENGTH: 21
<212> TYPE: DNA
<213> ORGANISM: Escherichia coli

<400> SEQUENCE: 5
gaaccatgga cgttattgca a                                               21

<210> SEQ ID NO 6
<211> LENGTH: 30
<212> TYPE: DNA
<213> ORGANISM: Escherichia coli

<400> SEQUENCE: 6
gaaccgcggt tattttttgc tttcttcttt                                      30

<210> SEQ ID NO 7
<211> LENGTH: 99
<212> TYPE: DNA
<213> ORGANISM: Escherichia coli

<400> SEQUENCE: 7
atgtctttat ctcgtcgtca attcattcaa gcttctggta ttgctttatg tgctggtgct     60
gttcctttaa aggcttctgc tatgaacgtt attgcaata                            99

<210> SEQ ID NO 8
<211> LENGTH: 60
<212> TYPE: DNA
<213> ORGANISM: Escherichia coli

<400> SEQUENCE: 8
ttgaatgaat tgacgacgag ataaagacat ggcacccctt gtattactgt ttatgtaagc     60

<210> SEQ ID NO 9
<211> LENGTH: 35
<212> TYPE: DNA
<213> ORGANISM: Escherichia coli

<400> SEQUENCE: 9
ttcggatccc ctgaatcgcc ccatcatcca gccag                                35

<210> SEQ ID NO 10
<211> LENGTH: 35
<212> TYPE: DNA
<213> ORGANISM: Escherichia coli

<400> SEQUENCE: 10
gttgcatgct tattttttgc tttcttcttt caata                                35

<210> SEQ ID NO 11
<211> LENGTH: 120
<212> TYPE: DNA
<213> ORGANISM: Bacillus subtilis
```

```
<400> SEQUENCE: 11
atgagaagca aaaaattgtg gatcagcttg ttgtttgcgt taacgttaat ctttacgatg        60
gcgttcagca acatgtctgc gcaggctatg aacgttattg caatattgaa tcacatgggg       120
```

<210> SEQ ID NO 12
<211> LENGTH: 60
<212> TYPE: DNA
<213> ORGANISM: Bacillus subtilis

```
<400> SEQUENCE: 12
caagctgatc cacaatttt tgcttctcat ggcacccctt gtattactgt ttatgtaagc         60
```

<210> SEQ ID NO 13
<211> LENGTH: 39
<212> TYPE: PRT
<213> ORGANISM: Escherichia coli

<400> SEQUENCE: 13

Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala
        35

<210> SEQ ID NO 14
<211> LENGTH: 27
<212> TYPE: PRT
<213> ORGANISM: Escherichia coli

<400> SEQUENCE: 14

Met Ser Leu Ser Arg Arg Gln Phe Ile Gln Ala Ser Gly Ile Ala Leu
1               5                   10                  15

Cys Ala Gly Ala Val Pro Leu Lys Ala Ser Ala
            20                  25

<210> SEQ ID NO 15
<211> LENGTH: 48
<212> TYPE: PRT
<213> ORGANISM: Bacillus subtilis

<400> SEQUENCE: 15

Met Ala Tyr Asp Ser Arg Phe Asp Glu Trp Val Gln Lys Leu Lys Glu
1               5                   10                  15

Glu Ser Phe Gln Asn Asn Thr Phe Asp Arg Arg Lys Phe Ile Gln Gly
            20                  25                  30

Ala Gly Lys Ile Ala Gly Leu Ser Leu Gly Leu Thr Ile Ala Gln Ser
        35                  40                  45

<210> SEQ ID NO 16
<211> LENGTH: 34
<212> TYPE: PRT
<213> ORGANISM: Bacillus subtilis

<400> SEQUENCE: 16

Met Lys Phe Val Lys Arg Arg Thr Thr Ala Leu Val Thr Thr Leu Met
1               5                   10                  15

Leu Ser Val Thr Ser Leu Phe Ala Leu Gln Pro Ser Ala Lys Ala Ala
            20                  25                  30

Glu His

<210> SEQ ID NO 17
<211> LENGTH: 30
<212> TYPE: PRT
<213> ORGANISM: Arthrobacter globiformis

<400> SEQUENCE: 17

Met Met Asn Leu Ser Arg Arg Thr Leu Leu Thr Thr Gly Ser Ala Ala
1               5                   10                  15

Thr Leu Ala Tyr Ala Leu Gly Met Ala Gly Ser Ala Gln Ala
            20                  25                  30

<210> SEQ ID NO 18
<211> LENGTH: 25
<212> TYPE: PRT
<213> ORGANISM: Corynebacterium ammoniagenes

<400> SEQUENCE: 18

Met Lys Arg Met Lys Ser Leu Ala Ala Ala Leu Thr Val Ala Gly Ala
1               5                   10                  15

Met Leu Ala Ala Pro Val Ala Thr Ala
            20                  25

<210> SEQ ID NO 19
<211> LENGTH: 48
<212> TYPE: PRT
<213> ORGANISM: Corynebacterium glutamicum

<400> SEQUENCE: 19

Met Pro Ser Phe Lys Ser Ala Arg Trp Arg Met Asn Arg Arg Leu Phe
1               5                   10                  15

Leu Gly Thr Ser Ala Ala Ile Ile Ala Val Gly Val Leu Gly Gly
            20                  25                  30

Val Gln Val Val Pro Tyr Ile Ser Ser Gly Glu Ile Gln Thr Ser Ala
        35                  40                  45

<210> SEQ ID NO 20
<211> LENGTH: 35
<212> TYPE: PRT
<213> ORGANISM: Corynebacterium glutamicum

<400> SEQUENCE: 20

Met Thr Ser Ser Phe Ser Arg Arg Gln Phe Leu Leu Gly Gly Leu Val
1               5                   10                  15

Leu Ala Gly Thr Gly Ala Val Ala Ala Cys Thr Ser Asp Pro Gly Pro
            20                  25                  30

Ala Ala Ser
        35

<210> SEQ ID NO 21
<211> LENGTH: 35
<212> TYPE: PRT
<213> ORGANISM: Corynebacterium glutamicum

<400> SEQUENCE: 21

Met Thr Thr Pro Thr Ser Pro Leu Leu Pro Leu Ala Ser Asp Gly Cys
1               5                   10                  15

Gly Cys Cys Ala Pro Ser Thr Pro Ser Ala Thr Val Ser Ala Pro Ala
            20                  25                  30

Val Ala Ala

<210> SEQ ID NO 22
<211> LENGTH: 29
<212> TYPE: PRT
<213> ORGANISM: Corynebacterium glutamicum

<400> SEQUENCE: 22

Met Arg Arg Pro Val Ser Arg Arg Ala Ile Phe Ala Thr Ser Val Leu
1               5                   10                  15

Val Ala Gly Val Ser Ile Met Ser Pro Ser Ala Asn Ala
            20                  25

<210> SEQ ID NO 23
<211> LENGTH: 30
<212> TYPE: PRT
<213> ORGANISM: Corynebacterium glutamicum

<400> SEQUENCE: 23

Met Gln Ile Asn Arg Arg Gly Phe Leu Lys Ala Thr Ala Gly Leu Ala
1               5                   10                  15

Thr Ile Gly Ala Ala Ser Met Phe Met Pro Lys Ala Asn Ala
            20                  25                  30

<210> SEQ ID NO 24
<211> LENGTH: 31
<212> TYPE: PRT
<213> ORGANISM: Corynebacterium glutamicum

<400> SEQUENCE: 24

Val Arg Lys Gly Ile Ser Arg Val Leu Ser Val Ala Val Ala Ser Ser
1               5                   10                  15

Ile Gly Phe Gly Thr Val Leu Thr Gly Thr Gly Ile Ala Ala Ala
            20                  25                  30

<210> SEQ ID NO 25
<211> LENGTH: 35
<212> TYPE: PRT
<213> ORGANISM: Corynebacterium glutamicum

<400> SEQUENCE: 25

Met Ala Gln Ile Ser Arg Arg His Phe Leu Ala Ala Ala Thr Val Ala
1               5                   10                  15

Gly Ala Gly Ala Thr Leu Ala Ala Cys Ala Gly Thr Gly Gly Ser Thr
            20                  25                  30

Ser Ser Ser
        35

<210> SEQ ID NO 26
<211> LENGTH: 29
<212> TYPE: PRT
<213> ORGANISM: Corynebacterium glutamicum

<400> SEQUENCE: 26

Met Pro Gln Leu Ser Arg Arg Gln Phe Leu Gln Thr Thr Ala Val Thr
1               5                   10                  15

Ala Gly Leu Ala Thr Phe Leu Gly Thr Pro Ala Arg Ala
            20                  25

<210> SEQ ID NO 27
<211> LENGTH: 40
<212> TYPE: PRT

<213> ORGANISM: Corynebacterium glutamicum

<400> SEQUENCE: 27

Met Val Asn Thr Leu Asn Ser Lys Thr Val Asn Val Pro Arg Phe Ala
1               5                   10                  15

Arg Gly Val Val Ala Ala Ala Thr Ala Leu Phe Phe Gly Ala Leu Val
            20                  25                  30

Ser Leu Ala Pro Ser Ala Leu Ala
        35                  40

<210> SEQ ID NO 28
<211> LENGTH: 38
<212> TYPE: PRT
<213> ORGANISM: Corynebacterium glutamicum

<400> SEQUENCE: 28

Met Thr Gln Pro Ala Pro Met Cys Ser Arg Arg Met Phe Leu Leu Gly
1               5                   10                  15

Thr Ala Thr Thr Phe Ala Gly Ala Phe Leu Ala Ala Cys Gly Thr Glu
            20                  25                  30

Pro Asp Gln Glu Val Ala
        35

<210> SEQ ID NO 29
<211> LENGTH: 22
<212> TYPE: PRT
<213> ORGANISM: Corynebacterium glutamicum

<400> SEQUENCE: 29

Met Lys Asn Ser Lys Leu Leu Leu Ile Ala Ala Val Ser Thr Ala Ser
1               5                   10                  15

Ile Leu Leu Ala Ser Cys
            20

<210> SEQ ID NO 30
<211> LENGTH: 22
<212> TYPE: PRT
<213> ORGANISM: Corynebacterium glutamicum

<400> SEQUENCE: 30

Met Arg Thr Ser Arg Val Leu Ala Gly Ile Leu Ala Ala Thr Leu Thr
1               5                   10                  15

Val Ser Leu Ala Ala Cys
            20

<210> SEQ ID NO 31
<211> LENGTH: 24
<212> TYPE: PRT
<213> ORGANISM: Corynebacterium glutamicum

<400> SEQUENCE: 31

Val Ser Lys Ile Ser Thr Lys Leu Lys Ala Leu Ser Ala Val Leu Ser
1               5                   10                  15

Val Thr Thr Leu Val Ala Gly Cys
            20

<210> SEQ ID NO 32
<211> LENGTH: 28
<212> TYPE: PRT
<213> ORGANISM: Corynebacterium glutamicum

<400> SEQUENCE: 32

```
Met Phe Lys Leu Ser Lys Pro Ser Lys Ser Met Arg Val Ala Val Ser
1               5                   10                  15

Thr Leu Ala Ile Ser Thr Leu Ala Leu Val Gly Cys
            20                  25
```

<210> SEQ ID NO 33
<211> LENGTH: 22
<212> TYPE: PRT
<213> ORGANISM: Corynebacterium glutamicum

<400> SEQUENCE: 33

```
Met Thr Leu Lys Lys Ser Leu Ala Val Thr Thr Ala Ala Ala Leu Ala
1               5                   10                  15

Leu Ser Leu Ala Ala Cys
            20
```

<210> SEQ ID NO 34
<211> LENGTH: 23
<212> TYPE: PRT
<213> ORGANISM: Corynebacterium glutamicum

<400> SEQUENCE: 34

```
Met Ser Ile Ser Arg Thr Val Phe Gly Ile Ala Ala Thr Ala Ala Leu
1               5                   10                  15

Ser Ala Ala Leu Val Ala Cys
            20
```

<210> SEQ ID NO 35
<211> LENGTH: 29
<212> TYPE: PRT
<213> ORGANISM: Corynebacterium glutamicum

<400> SEQUENCE: 35

```
Val Arg Val Phe Arg Gly Arg Gly Ala Val Ala Gly Ser Phe Leu
1               5                   10                  15

Ala Val Leu Ala Ile Gly Ser Leu Ala Leu Thr Gly Cys
            20                  25
```

<210> SEQ ID NO 36
<211> LENGTH: 21
<212> TYPE: PRT
<213> ORGANISM: Corynebacterium glutamicum

<400> SEQUENCE: 36

```
Met Ala Asp Met Lys Lys Leu Leu Trp Thr Leu Pro Ile Leu Pro Leu
1               5                   10                  15

Val Leu Ala Gly Cys
            20
```

<210> SEQ ID NO 37
<211> LENGTH: 30
<212> TYPE: PRT
<213> ORGANISM: Brevibacterium sp.

<400> SEQUENCE: 37

```
Met Phe Asn Asn Arg Ile Arg Thr Ala Ala Leu Ala Gly Ala Leu Ala
1               5                   10                  15

Ile Ser Thr Ala Ala Ser Gly Ala Ala Ile Pro Ala Phe Ala
            20                  25                  30
```

<210> SEQ ID NO 38

```
<211> LENGTH: 40
<212> TYPE: PRT
<213> ORGANISM: Bacillus subtilis

<400> SEQUENCE: 38

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Met Asn Val
            20                  25                  30

Ile Ala Ile Leu Asn His Met Gly
        35                  40

<210> SEQ ID NO 39
<211> LENGTH: 31
<212> TYPE: PRT
<213> ORGANISM: Corynebacterium glutamicum

<400> SEQUENCE: 39

Met Arg Ile Arg Arg Arg Ala Leu Val Phe Ala Thr Met Ser Ala Val
1               5                   10                  15

Leu Cys Thr Ala Gly Phe Met Pro Ser Ala Gly Glu Ala Ala Ala
            20                  25                  30

<210> SEQ ID NO 40
<211> LENGTH: 21
<212> TYPE: PRT
<213> ORGANISM: Escherichia coli

<400> SEQUENCE: 40

Met Lys Lys Thr Ala Ile Ala Ile Ala Val Ala Leu Ala Gly Phe Ala
1               5                   10                  15

Thr Val Ala Gln Ala
            20

<210> SEQ ID NO 41
<211> LENGTH: 26
<212> TYPE: PRT
<213> ORGANISM: Escherichia coli

<400> SEQUENCE: 41

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 42
<211> LENGTH: 45
<212> TYPE: PRT
<213> ORGANISM: Escherichia coli

<400> SEQUENCE: 42

Met Lys Thr Lys Ile Pro Asp Ala Val Leu Ala Ala Glu Val Ser Arg
1               5                   10                  15

Arg Gly Leu Val Lys Thr Thr Ala Ile Gly Gly Leu Ala Met Ala Ser
            20                  25                  30

Ser Ala Leu Thr Leu Pro Phe Ser Arg Ile Ala His Ala
        35                  40                  45

<210> SEQ ID NO 43
<211> LENGTH: 45
<212> TYPE: PRT
<213> ORGANISM: Escherichia coli
```

<400> SEQUENCE: 43

Met Asn Asn Glu Glu Thr Phe Tyr Gln Ala Met Arg Arg Gln Gly Val
1               5                   10                  15

Thr Arg Arg Ser Phe Leu Lys Tyr Cys Ser Leu Ala Ala Thr Ser Leu
            20                  25                  30

Gly Leu Gly Ala Gly Met Ala Pro Lys Ile Ala Trp Ala
        35                  40                  45

<210> SEQ ID NO 44
<211> LENGTH: 117
<212> TYPE: DNA
<213> ORGANISM: Escherichia coli

<400> SEQUENCE: 44
atgaataata atgatttatt ccaagcttct cgtcgtcgtt tcttagctca attaggtggt      60
ttaactgttg ctggtatgtt aggtccttct ttattaactc ctcgtcgtgc tactgct       117

<210> SEQ ID NO 45
<211> LENGTH: 81
<212> TYPE: DNA
<213> ORGANISM: Escherichia coli

<400> SEQUENCE: 45
atgtctttat ctcgtcgtca attcattcaa gcttctggta ttgctttatg tgctggtgct      60
gttcctttaa aggcttctgc t                                                 81

<210> SEQ ID NO 46
<211> LENGTH: 144
<212> TYPE: DNA
<213> ORGANISM: Bacillus subtilis

<400> SEQUENCE: 46
atggcttatg attctcgttt cgatgagtgg gttcaaaagt taaggagga gtctttccaa       60 aataatactt tcgatcgtcg taagttcatt caaggtgctg gtaagattgc tggtttatct    120
ttaggtttaa ctattgctca atct                                             144

<210> SEQ ID NO 47
<211> LENGTH: 102
<212> TYPE: DNA
<213> ORGANISM: Bacillus subtilis

<400> SEQUENCE: 47
atgaagttcg ttaagcgtcg tactactgct ttagttacta ctttaatgtt atctgttact      60
tctttattcg ctttacaacc ttctgctaag gctgctgagc at                         102

<210> SEQ ID NO 48
<211> LENGTH: 90
<212> TYPE: DNA
<213> ORGANISM: Arthrobacter globiformis

<400> SEQUENCE: 48
atgatgaatt tatctcgtcg tactttatta actactggtt ctgctgctac tttagcttat      60
gctttaggta tggctggttc tgctcaagct                                       90

<210> SEQ ID NO 49
<211> LENGTH: 75
<212> TYPE: DNA
<213> ORGANISM: Corynebacterium ammoniagenes -continued

<400> SEQUENCE: 49
atgaagcgta tgaagtcttt agctgctgct ttaactgttg ctggtgctat gttagctgct    60
cctgttgcta ctgct                                                      75

<210> SEQ ID NO 50
<211> LENGTH: 144
<212> TYPE: DNA
<213> ORGANISM: Corynebacterium glutamicum

<400> SEQUENCE: 50
atgccttctt tcaagtctgc tcgttggcgt atgaatcgtc gtttattctt aggtacttct    60
gctgctatta ttgctgttgg tggtgtttta ggtggtgttc aagttgttcc ttatatttct   120
tctggtgaga ttcaaacttc tgct                                           144

<210> SEQ ID NO 51
<211> LENGTH: 105
<212> TYPE: DNA
<213> ORGANISM: Corynebacterium glutamicum

<400> SEQUENCE: 51
atgacttctt ctttctctcg tcgtcaattc ttattaggtg gtttagtttt agctggtact    60
ggtgctgttg ctgcttgtac ttctgatcct ggtcctgctg cttct                   105

<210> SEQ ID NO 52
<211> LENGTH: 105
<212> TYPE: DNA
<213> ORGANISM: Corynebacterium glutamicum

<400> SEQUENCE: 52
atgactactc ctacttctcc tttattacct ttagcttctg atggttgtgg ttgttgtgct    60
ccttctactc cttctgctac tgtttctgct cctgctgttg ctgct                   105

<210> SEQ ID NO 53
<211> LENGTH: 87
<212> TYPE: DNA
<213> ORGANISM: Corynebacterium glutamicum

<400> SEQUENCE: 53
atgcgtcgtc ctgtttctcg tcgtgctatt ttcgctactt ctgttttagt tgctggtgtt    60
tctattatgt ctccttctgc taatgct                                        87

<210> SEQ ID NO 54
<211> LENGTH: 90
<212> TYPE: DNA
<213> ORGANISM: Corynebacterium glutamicum

<400> SEQUENCE: 54
atgcaaatta atcgtcgtgg tttcttaaag gctactgctg gtttagctac tattggtgct    60
gcttctatgt tcatgcctaa ggctaatgct                                      90

<210> SEQ ID NO 55
<211> LENGTH: 93
<212> TYPE: DNA
<213> ORGANISM: Corynebacterium glutamicum

<400> SEQUENCE: 55
gttcgtaagg gtatttctcg tgtttttatct gttgctgttg cttcttctat tggtttcggt    60

```
actgttttaa ctggtactgg tattgctgct gct                                  93

<210> SEQ ID NO 56
<211> LENGTH: 105
<212> TYPE: DNA
<213> ORGANISM: Corynebacterium glutamicum

<400> SEQUENCE: 56
atggctcaaa tttctcgtcg tcatttctta gctgctgcta ctgttgctgg tgctggtgct    60
actttagctg cttgtgctgg tactggtggt tctacttctt cttct                   105

<210> SEQ ID NO 57
<211> LENGTH: 87
<212> TYPE: DNA
<213> ORGANISM: Corynebacterium glutamicum

<400> SEQUENCE: 57
atgcctcaat tatctcgtcg tcaattctta caaactactg ctgttactgc tggtttagct    60
actttcttag gtactcctgc tcgtgct                                        87

<210> SEQ ID NO 58
<211> LENGTH: 120
<212> TYPE: DNA
<213> ORGANISM: Corynebacterium glutamicum

<400> SEQUENCE: 58
atggttaata ctttaaattc taagactgtt aatgttcctc gtttcgctcg tggtgttgtt    60
gctgctgcta ctgctttatt cttcggtgct ttagttcttt tagctccttc tgctttagct   120

<210> SEQ ID NO 59
<211> LENGTH: 114
<212> TYPE: DNA
<213> ORGANISM: Corynebacterium glutamicum

<400> SEQUENCE: 59
atgactcaac ctgctcctat gtgttctcgt cgtatgttct tattaggtac tgctactact    60
ttcgctggtg ctttcttagc tgcttgtggt actgagcctg atcaagaggt tgct         114

<210> SEQ ID NO 60
<211> LENGTH: 66
<212> TYPE: DNA
<213> ORGANISM: Corynebacterium glutamicum

<400> SEQUENCE: 60
atgaagaatt ctaagttatt attaattgct gctgtttcta ctgcttctat tttattagct    60
tcttgt                                                               66

<210> SEQ ID NO 61
<211> LENGTH: 66
<212> TYPE: DNA
<213> ORGANISM: Corynebacterium glutamicum

<400> SEQUENCE: 61
atgcgtactt ctcgtgtttt agctggtatt ttagctgcta ctttaactgt ttctttagct    60
gcttgt                                                               66

<210> SEQ ID NO 62
<211> LENGTH: 72
<212> TYPE: DNA
<213> ORGANISM: Corynebacterium glutamicum
```

<400> SEQUENCE: 62
gtttctaaga tttctactaa gttaaaggct ttatctgctg ttttatctgt tactactttta    60 gttgctggtt gt    72

<210> SEQ ID NO 63
<211> LENGTH: 84
<212> TYPE: DNA
<213> ORGANISM: Corynebacterium glutamicum

<400> SEQUENCE: 63
atgttcaagt tatctaagcc ttctaagtct atgcgtgttg ctgtttctac tttagctatt    60
tctactttag ctttagttgg ttgt    84

<210> SEQ ID NO 64
<211> LENGTH: 66
<212> TYPE: DNA
<213> ORGANISM: Corynebacterium glutamicum

<400> SEQUENCE: 64
atgactttaa agaagtcttt agctgttact actgctgctg ctttagcttt atctttagct    60
gcttgt    66

<210> SEQ ID NO 65
<211> LENGTH: 69
<212> TYPE: DNA
<213> ORGANISM: Corynebacterium glutamicum

<400> SEQUENCE: 65
atgtctattt ctcgtactgt tttcggtatt gctgctactg ctgctttatc tgctgcttta    60
gttgcttgt    69

<210> SEQ ID NO 66
<211> LENGTH: 87
<212> TYPE: DNA
<213> ORGANISM: Corynebacterium glutamicum

<400> SEQUENCE: 66
gttcgtgttt tccgtggtcg tcgtggtgct gttgctggtt ctttcttagc tgttttagct    60
attggttctt tagctttaac tggttgt    87

<210> SEQ ID NO 67
<211> LENGTH: 63
<212> TYPE: DNA
<213> ORGANISM: Corynebacterium glutamicum

<400> SEQUENCE: 67
atggctgata tgaagaagtt attatggact ttacctattt tacctttagt tttagctggt    60
tgt    63

<210> SEQ ID NO 68
<211> LENGTH: 90
<212> TYPE: DNA
<213> ORGANISM: Brevibacterium sp.

<400> SEQUENCE: 68
atgttcaata atcgtattcg tactgctgct ttagctggtg ctttagctat ttctactgct    60
gcttctggtg ctgctattcc tgctttcgct    90

<210> SEQ ID NO 69
<211> LENGTH: 120
<212> TYPE: DNA
<213> ORGANISM: Bacillus subtilis

<400> SEQUENCE: 69

```
atgcgttcta agaagttatg gatttctttta ttattcgctt taactttaat tttcactatg      60
gctttctcta atatgtctgc tcaagctatg aatgttattg ctattttaaa tcatatgggt     120
```

<210> SEQ ID NO 70
<211> LENGTH: 93
<212> TYPE: DNA
<213> ORGANISM: Corynebacterium glutamicum

<400> SEQUENCE: 70

```
atgcgtattc gtcgtcgtgc tttagttttc gctactatgt ctgctgtttt atgtactgct      60
ggtttcatgc cttctgctgg tgaggctgct gct                                    93
```

<210> SEQ ID NO 71
<211> LENGTH: 63
<212> TYPE: DNA
<213> ORGANISM: Escherichia coli

<400> SEQUENCE: 71

```
atgaagaaga ctgctattgc tattgctgtt gctttagctg gtttcgctac tgttgctcaa      60
gct                                                                    63
```

<210> SEQ ID NO 72
<211> LENGTH: 78
<212> TYPE: DNA
<213> ORGANISM: Escherichia coli

<400> SEQUENCE: 72

```
atgaagatta agactggtgc tcgtatttta gctttatctg ctttaactac tatgatgttc      60
tctgcttctg ctttagct                                                    78
```

<210> SEQ ID NO 73
<211> LENGTH: 135
<212> TYPE: DNA
<213> ORGANISM: Escherichia coli

<400> SEQUENCE: 73

```
atgaagacta agattcctga tgctgtttta gctgctgagg tttctcgtcg tggtttagtt      60
aagactactg ctattggtgg tttagctatg gcttcttctg ctttaacttt acctttctct     120
cgtattgctc atgct                                                      135
```

<210> SEQ ID NO 74
<211> LENGTH: 135
<212> TYPE: DNA
<213> ORGANISM: Escherichia coli

<400> SEQUENCE: 74

```
atgaataatg aggagacttt ctatcaagct atgcgtcgtc aaggtgttac tcgtcgttct      60
ttcttaaagt attgttcttt agctgctact tctttaggtt taggtgctgg tatggctcct     120
aagattgctt gggct                                                      135
```

<210> SEQ ID NO 75
<211> LENGTH: 34

```
<212> TYPE: DNA
<213> ORGANISM: Escherichia coli

<400> SEQUENCE: 75
gaagttccta tactttctag agaataggaa cttc                                34

<210> SEQ ID NO 76
<211> LENGTH: 70
<212> TYPE: DNA
<213> ORGANISM: Escherichia coli

<400> SEQUENCE: 76
cattttgtcc catgtgttgg gagggccctt ttttacctgg agatatgact gtgtaggctg    60
gagctgcttc                                                           70

<210> SEQ ID NO 77
<211> LENGTH: 70
<212> TYPE: DNA
<213> ORGANISM: Escherichia coli

<400> SEQUENCE: 77
cttatgagca aaaagggaa gtggcaagcc acttcccttg tacgagctaa catatgaata     60
tcctccttag                                                           70

<210> SEQ ID NO 78
<211> LENGTH: 70
<212> TYPE: DNA
<213> ORGANISM: Escherichia coli

<400> SEQUENCE: 78
ccacggtttg agcaggctat gattaaggaa ggattttcca ggaggaacac gtgtaggctg    60
gagctgcttc                                                           70

<210> SEQ ID NO 79
<211> LENGTH: 69
<212> TYPE: DNA
<213> ORGANISM: Escherichia coli

<400> SEQUENCE: 79
tcctttattt gttaacagca cgttactcgc ccggaagccg ctctggcaag catatgaata    60
tcctcctta                                                            69
```